US008967861B2

(12) United States Patent
Mizuno et al.

(10) Patent No.: US 8,967,861 B2
(45) Date of Patent: *Mar. 3, 2015

(54) RADIOGRAPHIC IMAGE DETECTION APPARATUS

(75) Inventors: Kouichi Mizuno, Kanagawa (JP); Yusuke Kitagawa, Kanagawa (JP)

(73) Assignee: Fujifilm Corporation, Tokyo (JP)

( * ) Notice: Subject to any disclaimer, the term of this patent is extended or adjusted under 35 U.S.C. 154(b) by 117 days.

This patent is subject to a terminal disclaimer.

(21) Appl. No.: 13/169,787

(22) Filed: Jun. 27, 2011

(65) Prior Publication Data

US 2012/0140900 A1    Jun. 7, 2012

(30) Foreign Application Priority Data

Apr. 4, 2011   (JP) .................................. 2011-082724

(51) Int. Cl.
*H01J 31/49*   (2006.01)
*A61B 6/00*   (2006.01)
*G03B 42/04*   (2006.01)

(52) U.S. Cl.
CPC .............. *A61B 6/4283* (2013.01); *A61B 6/4233* (2013.01); *G03B 42/047* (2013.01)
USPC ........................................... 378/189; 378/169

(58) Field of Classification Search
USPC .................. 378/163–166, 169, 189
See application file for complete search history.

(56) References Cited

U.S. PATENT DOCUMENTS

| | | | |
|---|---|---|---|
| 4,429,412 A * | 1/1984 | Pierce et al. ................... | 378/165 |
| 6,260,999 B1 * | 7/2001 | Wofford et al. ................ | 378/205 |
| 7,482,601 B2 * | 1/2009 | Lewis et al. ................. | 250/474.1 |
| 8,657,493 B2 * | 2/2014 | Mizuno et al. ................ | 378/189 |

| | | | |
|---|---|---|---|
| 2001/0050975 A1 * | 12/2001 | Nakajo ......................... | 378/182 |
| 2004/0149930 A1 | 8/2004 | Ando | |
| 2008/0239332 A1 | 10/2008 | Takada et al. | |
| 2009/0168956 A1 | 7/2009 | Lin | |

FOREIGN PATENT DOCUMENTS

| | | |
|---|---|---|
| CN | 1517787 A | 8/2004 |
| CN | 101274512 A | 10/2008 |

(Continued)

OTHER PUBLICATIONS

Japanese Notification of Reasons for Refusal dated Apr. 23, 2014, with English translation.

(Continued)

*Primary Examiner* — Hoon Song
(74) *Attorney, Agent, or Firm* — McGinn IP Law Group, PLLC

(57) ABSTRACT

A radiographic image detection apparatus includes a detection panel and a housing for containing the detection panel. The housing consists of a front surface member, a back surface member, and a carbon plate attached so as to cover an opening formed in the front surface member. The carbon plate is faced to the detection panel. To the carbon plate is adhered a transparent sheet having transmissivity to radiation and visible light. A first index and a second index are printed on an inner surface of the transparent sheet. The first index is a square-frame shaped index showing a radiation detection range of the detection panel. The second index is a cross-shaped index showing a center position of the radiation detection range. The first and second indices are formed of non-metallic UV curable ink having no radiation shielding properties.

19 Claims, 4 Drawing Sheets

(56) References Cited

FOREIGN PATENT DOCUMENTS

| JP | 62-129841 A | 6/1987 |
| JP | 10-001651 | 1/1998 |
| JP | 10-187043 | 7/1998 |
| JP | H 10-290797 A | 11/1998 |
| JP | 2006-006424(A) | 1/2006 |
| JP | 3130445 | 3/2007 |
| JP | 2009-083208 A | 4/2009 |
| JP | 2010-039267 A | 2/2010 |
| JP | 2010-085206 A | 4/2010 |
| JP | 2010-145720 A | 7/2010 |

OTHER PUBLICATIONS

Chinese First Notification of Office Action dated Jun. 5, 2014.
Japanese Office Action dated Oct. 1, 2014 with English Translation.

* cited by examiner

RADIOGRAPHIC IMAGE DETECTION APPARATUS

FIELD OF THE INVENTION

The present invention relates to a radiographic image detection apparatus for generating a radiographic image of a subject by detecting intensity distribution of radiation.

BACKGROUND OF THE INVENTION

Recently, in a medical field, an X-ray image detection apparatus provided with a detection panel for converting X rays that have been transmitted through a human body into electrical signals and outputting the electrical signals as images instead of radiation films such as X-ray films has been in widespread use. As the detection panel, there are an indirect-conversion type detection panel and a direct-conversion type detection panel. In the indirect-conversion type detection panel, X rays are converted into visible light by phosphors, and the visible light is converted into electric charges by photoelectric conversion elements. In the direct-conversion type detection panel, the X rays are directly converted into electric charges by a photoconductor layer.

The detection panel is contained in a housing. To a surface of the housing at the side nearer to the X-ray generator is attached a surface plate made of carbon-based material having low X-ray absorptivity such as carbon fiber, so that the X rays are efficiently transmitted through the detection panel. On the surface plate are formed a square-frame shaped index as a first index showing a detection range of the detection panel, and a cross-shaped index as a second index showing a center position of the detection range of the detection panel, as disclosed in Japanese Patent Laid-Open Publication No. 2006-6424, for example. Alignment between the detection range of the detection panel and an irradiation field of the X-ray generator is performed using the first and second indices. Additionally, the first and second indices are used for positioning of a subject (human body), so that the subject to be imaged is included within the detection range.

In a radiographic image detection apparatus disclosed in Japanese Patent Laid-Open Publication No. 2006-6424, the indices are generally directly printed on the surface plate by using pigment. Therefore, due to repeated contact with a radiographer and the subject, the indices unfavorably suffer from deterioration such as abrasion and peeling.

SUMMARY OF THE INVENTION

In view of the above, an object of the present invention is to provide a radiographic image detection apparatus capable of preventing deterioration of indices.

In order to achieve the above and other objects, a radiographic image detection apparatus of the present invention includes a detector, a housing, and a transparent sheet. The detector detects radiation to generate a radiographic image. The housing contains the detector. The transparent sheet is disposed so as to cover at least part of a surface of the housing. On an inner surface of the transparent sheet is formed an index showing at least one of a detection range of the detector and a center position of the detection range.

The index is preferably formed of a nonmetallic material. UV curable ink is preferable. The UV curable ink is preferably printed by an inkjet printer. It is preferable that, a portion of the housing, which is faced to the detector, is formed of a carbon plate, and an outer surface of the carbon plate is covered with a transparent sheet. The transparent sheet is preferably adhered to the carbon plate by using an adhesive.

The detector is preferably an indirect-conversion type flat panel detector in which the radiation is converted into visible light by phosphors, and the visible light is converted into electric charges by photoelectric conversion elements. The detector also may be a direct-conversion type flat panel detector for directly converting the radiation into electric charges by a photoconductor layer. Further, the radiographic image detection apparatus is preferably portable.

A radiographic image detection apparatus of the present invention includes a detector, a circuit board, a base plate, a housing, and a transparent sheet. The detector detects radiation to generate a radiographic image. The circuit board controls the detector. The detector is attached to one of surfaces of the base plate, and the circuit board is attached to the other of the surfaces of the base plate. The base plate is fixed to the housing. The housing contains the detector, the circuit board, and the base plate. The transparent sheet is disposed so as to cover at least part of a surface of the housing. An index showing at least one of a detection range of the detector and a center position of the detection range is formed on an inner surface of the transparent sheet.

According to the radiographic image detection apparatus of the present invention, since the index showing at least one of the detection range and the center position of the detection range is formed on the inner surface of the transparent sheet, the index is not exposed to the outside, and thus deterioration of the index can be prevented. Additionally, since the index is formed of the nonmetallic material, it is possible to form a radiographic image in which no indices appear.

DESCRIPTION OF THE DRAWINGS

The above objects and advantages of the present invention will become easily understood by one of ordinary skill in the art when the following detailed description of the preferred embodiments would be read in connection with the accompanying drawings, wherein.

DESCRIPTION OF THE PREFERRED EMBODIMENTS

Figure 1:
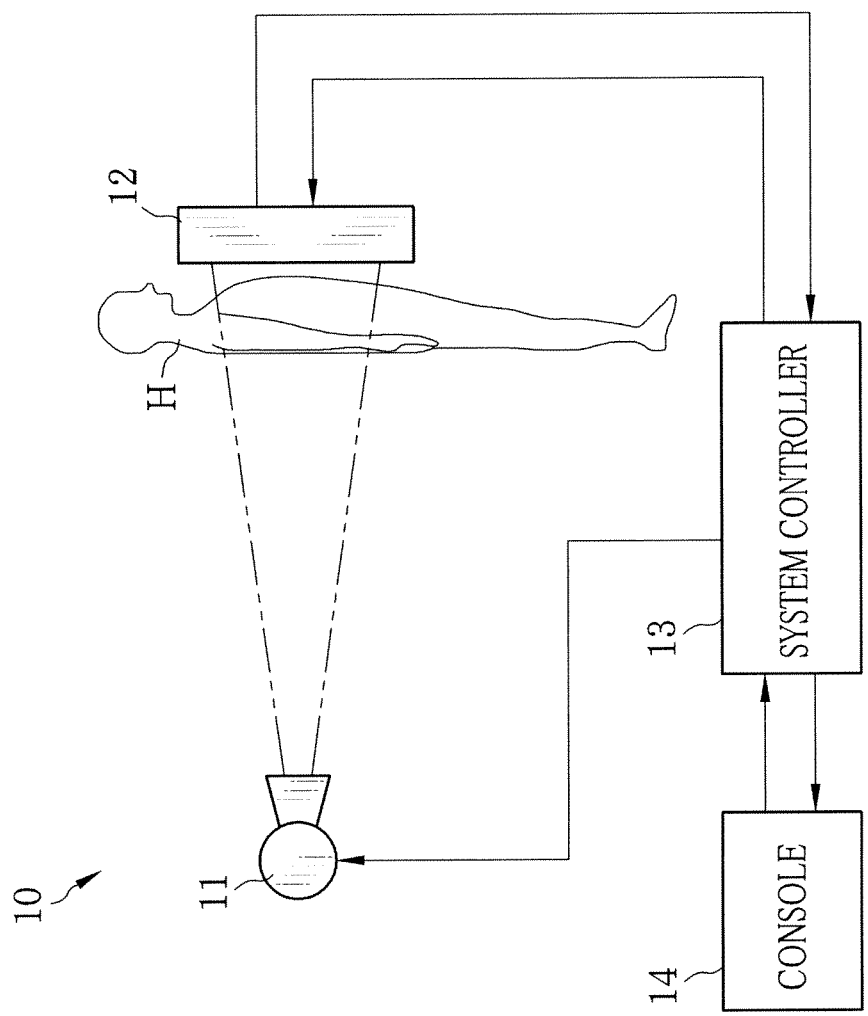
FIG. 1 is an explanatory view showing a radiographic imaging system.

In FIG. 1, a radiographic imaging system 10 of the present invention includes a radiation generator 11 for generating radiation such as X rays, a radiographic image detection apparatus 12, a system controller 13 for controlling the radiation generator 11 and the radiographic image detection apparatus 12, and a console 14. The radiographic image detection apparatus 12 detects radiation that has been transmitted through a subject (human body) H to obtain a radiographic image. The console 14 inputs imaging conditions such as tube voltage, tube current, and exposure time, and operation instructions such as imaging instructions to the system controller 13.

The radiation generator 11 is provided with a radiation tube having a cathode filament and an anode target. High voltage is applied between the cathode and the anode. Electrons emitted from the filament collide with the target to generate radiation.

Based on the imaging conditions and the imaging instructions received from the console 14, the system controller 13 controls the radiation generator 11 and the radiographic image detection apparatus 12 such that they operate in synchronization with each other. Data of the radiographic image outputted from the radiographic image detection apparatus 12 is transferred through the system controller 13 to the console 14. Data of the radiographic image received by the console 14 is outputted to a monitor and a data storage device such as an image server connected through a local hard disk and a communication network.

The radiographic image detection apparatus 12 is, for example, a portable electronic device, and referred to as an electronic cassette, that is mounted to a stand for upright imaging (not shown) having a pillar standing upright on the floor such that an incident surface on which radiation is made incident is in a vertical state. The radiographic image detection apparatus 12 can move up and down along the pillar such that the height thereof is adjustable in accordance with the body part to be imaged such as chest and abdominal. The height of the radiation generator 11 is also adjusted to the height of the radiographic image detection apparatus 12.

Figure 2:
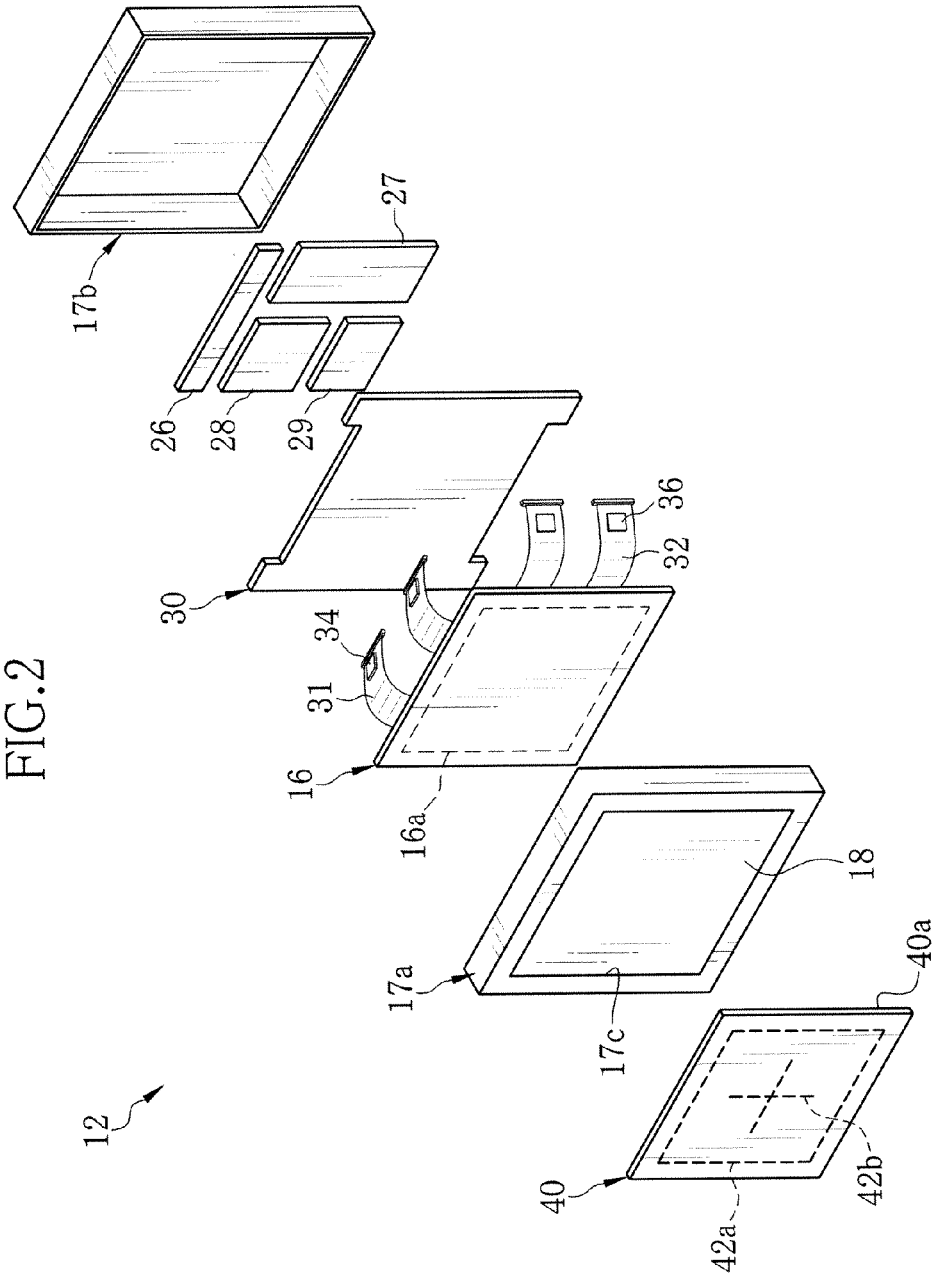
FIG. 2 is an exploded perspective view showing a radiographic image detection apparatus.
Figure 3:
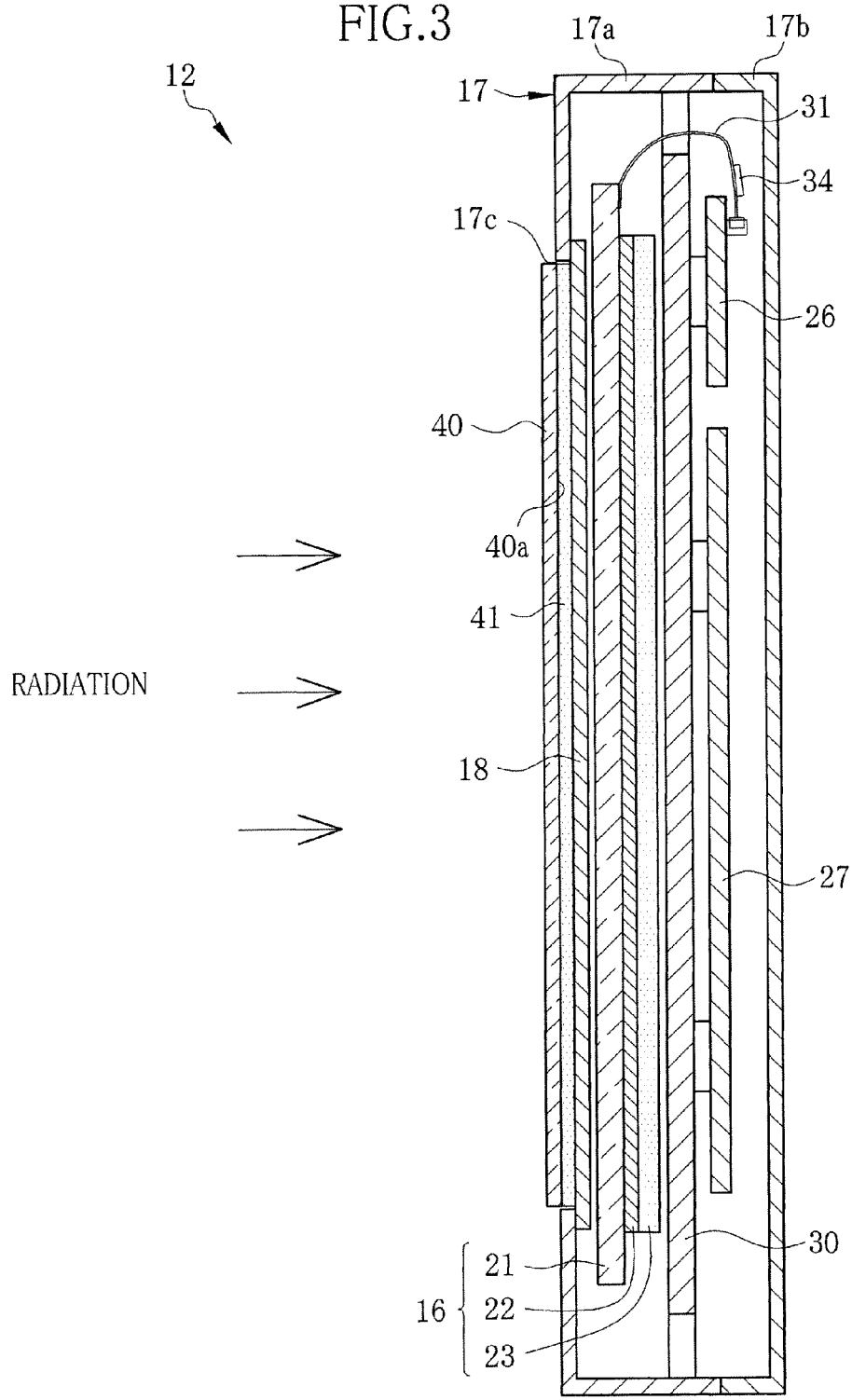
FIG. 3 is a cross-sectional view showing the radiographic image detection apparatus.

As shown in FIGS. 2 and 3, the radiographic image detection apparatus 12 includes a detection panel 16 and a housing 17 for containing the detection panel 16. An outer cover (not-shown) is provided around the housing 17. The housing 17 consists of a front surface member 17a for covering a front side of the detection panel 16 including the incident surface on which radiation is made incident, a back surface member 17b for covering a back side of the detection panel 16, and a carbon plate 18 having a size corresponding to a radiation detection range 16a of the detection panel 16. The front surface member 17a and the back surface member 17b are made of metal, through which the transmittance of the radiation is low, such as stainless. The front surface member 17a has an opening 17c in the shape of square. The carbon plate 18 is attached to the front surface member 17a so as to cover the opening 17c. The transmittance of the radiation through the carbon plate 18 is high. The radiation that has been transmitted through the carbon plate 18 is made incident on the detection panel 16.

The detection panel 16 consists of a glass substrate 21, a detection element array 22, and a scintillator 23, and is referred to as a flat panel detector (FPD). The glass substrate 21 has transmissivity to the radiation and insulation properties. The detection element array 22 includes thin film transistors (TFTs) as switching elements and photodiodes as photoelectric conversion elements, which are arranged in a matrix on the glass substrate 21. The glass substrate 21 and the detection element array 22 constitute a so-called active matrix substrate.

The scintillator 23 contains phosphors such as cesium iodide (CsI) and gadolinium oxysulfide (GOS), and emits visible light corresponding to the amount of radiation made incident thereon. The scintillator 23 is in the shape of a sheet applied with the phosphors, and adhered with use of an adhesive. The scintillator 23 may be a phosphor layer obtained by depositing the phosphors.

The photodiode is formed of amorphous silicon (a-Si), for example, and generates electric charges in response to the visible light. When being powered on, the TFTs read out electric charges generated by the photodiode on a signal line (not shown) provided for each column of the detection element array 22.

The detection panel 16 is of a so-called back illuminated type, in which the radiation is made incident on the scintillator 23 through the glass substrate 21 and the detection element array 22. A photo-detection surface of the detection element array 22 and the scintillator 23 are faced to each other. In the detection panel 16 of the back illuminated type, the radiation made incident on the glass substrate 21 is transmitted through the detection element array 22 to be made incident on the scintillator 23, and then visible light emitted from the scintillator 23 is received by the detection element array 22. The amount of light emitted from the scintillator 23 becomes largest at the side of the incident surface on which the radiation is made incident (namely at the side nearer to the detection element array 22), and therefore high detection efficiency can be achieved.

At the back surface side (namely at the side nearer to the scintillator 23) of the detection panel 16 is provided a base plate 30 to which the detection panel 16 and circuit boards 26 to 29 are mounted. The detection panel 16 is attached to a front surface of the base plate 30, and the circuit boards 26 to 29 are attached to the back surface thereof. The base plate 30 is made of stainless, for example, and fixed to the housing 17.

The circuit board 26 is provided with a driving circuit for driving the TFTs of the detection element array 22. The circuit board 27 is provided with an analogue-digital (A/D) conversion circuit. The A/D conversion circuit converts analog signals outputted from an IC chip 36, which is to be described later, into digital signals.

The circuit board 28 is provided with a control circuit. The control circuit controls the respective components of the radiographic image detection apparatus 12, and controls communication with an external device. The circuit board 29 is provided with a power circuit. The power circuit has circuit elements such as an AC/DC converter for converting alternate current (AC) to direct current (DC) and a DC/DC converter for converting direct voltage into voltage necessary for operation of each of the circuits, and supplies electric power to each of the components.

The circuit board 26 is connected to the detection panel 16 through a flexible cable 31, and the circuit board 27 is connected to the detection panel 16 through a flexible cable 32. An IC chip 34 is mounted on the flexible cable 31, and the IC chip 36 is mounted on the flexible cable 32.

The IC chip 34 is provided with a shift resistor for constituting part of the driving circuit for driving the TFTs. The IC chip 36 is an ASIC (Application Specific Integrated Circuit) constituting a readout circuit. The readout circuit includes a charge amplifier for converting signal charges read out from the detection panel 16 into voltage signals, and a multiplexer for selecting the signal lines formed for each column of the detection element array 22 in sequence and outputting the voltage signals of each column to the A/D conversion circuit.

To the surface of the carbon plate 18 exposed through the opening 17c of the housing 17 is adhered a transparent sheet 40 having transmissivity to the radiation and the visible light with use of an adhesive 41. The transparent sheet 40 is formed of polycarbonate and polyethylene terephthalate (PET), for example. The transparent sheet 40 has a size slightly larger than that of the opening 17c, and is attached to the carbon plate 18 so as to cover the opening 17c. The adhesive 41 has transmissivity to the radiation.

Figure 4:
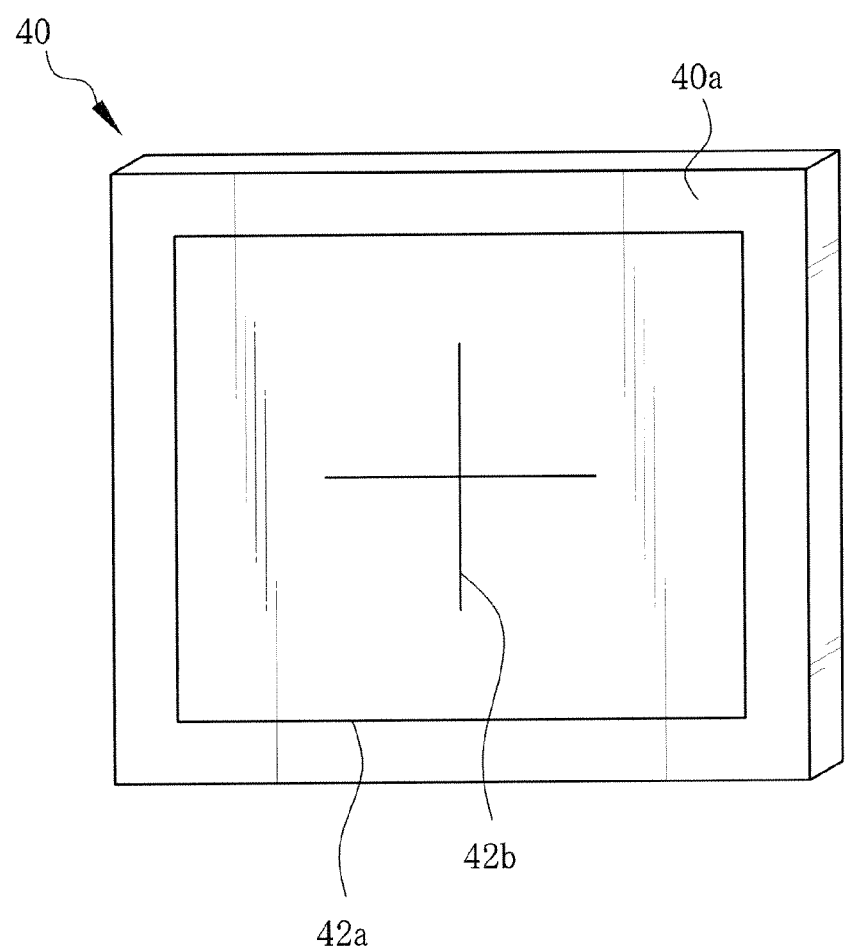
FIG. 4 is a view showing an inner surface of a transparent sheet.

As shown in FIGS. 2 and 4, a first index 42a and a second index 42b are printed on an inner surface 40a of the transparent sheet 40. The inner surface 40a is faced to the carbon plate 18. The first index 42a is a square-frame shaped index showing the radiation detection range 16a of the detection panel 16. The second index 42b is a cross-shaped index showing a center position of the radiation detection range 16a of the detection panel 16.

The first and second indices 42a and 42b are formed of nonmetallic ink not having radiation shielding properties. The nonmetallic ink is preferably UV curable ink, which is cured and stabilized by polymerization reaction when being applied with UV light (ultraviolet rays). As the UV curable ink is used "UV INK BLACK (product name): SPC-0371K-2 (product code)" commercialized by MIMAKI ENGINEERING CO., LTD. (URL: http://www.mimaki.co.jp/japanese/sup/supply/blank_ujf.php), or the like, for example.

The UV curable ink consists of liquid monomers (low molecules) and pigment. The liquid monomers are combined together upon being irradiated with UV light, and become polymer (high molecules). As coating of polymer resin forms a printed image on the surface of a base material, it is possible to perform printing directly on the transparent sheet 40 made of plastic such as polycarbonate and PET that is a non-water-absorbing material. The printing with use of the UV curable ink is performed by an inkjet printer. The UV curable ink is applied with UV light after the printing. Since the UV curable ink is cured promptly by the irradiation of the UV light, it is not necessary to dry the UV curable ink for many hours, and it becomes possible to decrease adhesion of foreign substances to the ink.

Note that, the transparent sheet 40 does not have to be completely transparent to the visible light. As far as the first and second indices 42a and 42b are visible from the side of the radiographic image detection apparatus 12, the transparency level of the transparent sheet 40 is sufficient.

Hereinafter, an operation of the above embodiment is described. Firstly, the radiographic image detection apparatus 12 is mounted to a stand for upright imaging. Then, a radiographer or the like adjusts the position of each of the radiation generator 11 and the stand for upright imaging by using the first and second indices 42a and 42b, such that the irradiation field of the radiation generator 11 and the radiation detection range 16a of the detection panel 16 approximately correspond with each other. Then, the position of the subject H is adjusted by using the first and second indices 42a and 42b, such that the body part of the subject H to be imaged is included within the radiation detection range 16a of the detection panel 16.

The console 14 is used to set the imaging conditions. After the subject H is located in an image capture position, the console 14 gives imaging start instruction to the system controller 13. The system controller 13 instructs the radiation generator 11 to irradiate the radiation toward the subject H, and instructs the detection panel 16 to detect the radiation so as to obtain the radiographic image of the subject H. The radiographic image is displayed on the monitor.

Since the first and second indices 42a and 42b are formed of the nonmetallic UV curable ink or the like, the radiation is not blocked by the first and second indices 42a and 42b, and the first and second indices 42a and 42b do not appear in the radiographic image. Accordingly, the risk of the presence of an affected part being overlooked from the radiographic image is decreased.

Additionally, since the first and second indices 42a and 42b are formed on the inner surface 40a of the transparent sheet 40, the first and second indices 42a and 42b do not suffer from deterioration such as abrasion and peeling. Therefore, it becomes unnecessary to form a protective layer such as overcoat, thus achieving decrease in cost. Further, the first and second indices 42a and 42b are formed on the transparent sheet 40 which is formed of inexpensive resin, and therefore, in comparison with the case where the first and second indices 42a and 42b are directly formed on the carbon plate 18 which is expensive, the production risk can be decreased more.

Additionally, since the transparent sheet 40 has insulation properties, the carbon plate 18 is electrically insulated from the outside.

Note that it is preferable that the transparent sheet 40 has been subjected to embossing or hard coating so as to be difficult to damage. Additionally, it is also preferable that indices similar to the first and second indices 42a and 42b, which are in the form of concavity and convexity, are formed on an outer surface of the transparent sheet 40, which is at the side nearer to the radiation generator 11, such that the position of the indices can be recognized by fingers at the time of adjusting the position of the radiographic image detection apparatus 12.

Further, although the first index 42a is formed in the shape of square frame and the second index 42b is formed in the shape of cross in the above embodiment, they are not limited to lines and may be formed by dots or the like. Additionally, inks of different colors may be used to paint the areas of the transparent sheet 40 with different colors, so as to show the radiation detection range 16a and the center position thereof.

Further, the first index 42a and second index 42b may be displayed by dots or the like instead of the lines. Additionally, inks of different colors may be used to paint the areas of the transparent sheet 40 with different colors, so as to show the radiation detection range 16a and the center position thereof.

Furthermore, although the radiographic image detection apparatus 12 is mounted to the stand for upright imaging in the above embodiment, as a matter of course, the radiographic image detection apparatus 12 may be installed on a bed for supine imaging, such that the incident surface thereof is aligned with an approximately horizontal direction.

Furthermore, although the detection panel 16 is the indirect-conversion type FPD, in which the radiation is converted into visible light by phosphors, and the visible light is converted into electric charges by photoelectric conversion elements, in the above embodiment, the present invention is not limited thereto. Instead of the indirect-conversion type FPD, there may be used a direct-conversion type FPD, in which the radiation is directly converted into electric charges by a photoconductor layer such as amorphous selenium (a-Se).

Various changes and modifications are possible in the present invention and may be understood to be within the present invention.

What is claimed is:

1. A radiographic image detection apparatus comprising:
   a detector for detecting radiation to generate a radiographic image;
   a housing for containing said detector;
   a transparent sheet, having transmissivity to visible light, disposed so as to cover at least part of a surface of said housing; and
   an index formed on an inner surface of said transparent sheet, said index showing at least one of a detection range of said detector and a center position of said detection range,
   wherein said index is formed of nonmetallic ink not having radiation shielding properties.

2. A radiographic image detection apparatus as defined in claim 1, wherein said index comprises UV curable ink.

3. A radiographic image detection apparatus as defined in claim 2, wherein said UV curable ink is printed by an inkjet printer.

4. A radiographic image detection apparatus as defined in claim 1, wherein a portion of said housing, which is faced to said detector, comprises a carbon plate, and an outer surface of said carbon plate is provided with said transparent sheet.

5. A radiographic image detection apparatus as defined in claim 4, wherein said carbon plate is adhered to the inner surface of said transparent sheet on which said index is formed via an adhesive.

6. A radiographic image detection apparatus as defined in claim 1, wherein said detector comprises an indirect-conversion type flat panel detector in which said radiation is converted into visible light by phosphors, and said visible light is converted into electric charges by photoelectric conversion elements.

7. A radiographic image detection apparatus as defined in claim 1, wherein said detector comprises a direct-conversion type flat panel detector for directly converting said radiation into electric charges by a photoconductor layer.

8. A radiographic image detection apparatus as defined in claim 1, being portable.

9. A radiographic image detection apparatus comprising:
a detector for detecting radiation to generate a radiographic image;
a circuit board for controlling said detector;
a base plate, one of surfaces of said base plate being provided with said detector, and the other surfaces of said base plate being provided with said circuit board;
a housing to which said base plate is fixed, said housing containing said detector, said circuit board, and said base plate;
a transparent sheet, having transmissivity to visible light, disposed so as to cover at least part of a surface of said housing; and
an index formed on an inner surface of said transparent sheet, said index showing at least one of a detection range of said detector and a center position of said detection range,
wherein said index is formed of nonmetallic ink not having radiation shielding properties.

10. A radiographic image detection apparatus as defined in claim 1, wherein a transparency level of the transparent sheet is configured such that the index is visible.

11. A radiographic image detection apparatus as defined in claim 1, wherein the transparent sheet comprises a resin material.

12. A radiographic image detection apparatus as defined in claim 5, wherein the transparent sheet comprises an insulating material.

13. A radiographic image detection apparatus as defined in claim 12, wherein the transparent sheet is configured so as to insulate the outer surface of the carbon plate.

14. A radiographic image detection apparatus as defined in claim 1, wherein the transparent sheet has transmissivity to radiation.

15. A radiographic image detection apparatus as defined in claim 1, wherein said index is visible from an outer surface of said transparent sheet.

16. A radiographic image detection apparatus as defined in claim 2, wherein said UV curable ink consists of liquid monomers and pigment.

17. A radiographic image detection apparatus as defined in claim 5, wherein the adhesive has transmissivity to the radiation.

18. A radiographic image detection apparatus as defined in claim 1, wherein the transparent sheet is embossed or hard coated.

19. A radiographic image detection apparatus as defined in claim 1, wherein said housing comprises an opening,
wherein a portion of said housing, which is faced to said detector, comprises a carbon plate, and an outer surface of said carbon plate exposed through said opening is provided with said transparent sheet,
wherein the transparent sheet is larger than the opening, and
wherein said carbon plate is adhered to the inner surface of said transparent sheet on which said index is formed via an adhesive provided in the opening of the housing.

\* \* \* \* \*